United States Patent [19]
Kato et al.

[11] Patent Number: 5,968,977
[45] Date of Patent: Oct. 19, 1999

[54] KETONITRILE DERIVATIVES AND ANTIBACTERIAL AGENT AND DRUGS CONTAINING THE SAME

[75] Inventors: Shozo Kato, Tokuyama; Hidenobu Itahana, Tokyo; Masao Yamaguchi, Tokuyama; Makiko Furuki, Tokyo; Seiji Nagata; Toshio Kitajima, both of Tokuyama, all of Japan

[73] Assignee: Tokuyama Corporation, Tokuyama, Japan

[21] Appl. No.: 08/973,715

[22] PCT Filed: Dec. 28, 1995

[86] PCT No.: PCT/JP95/02751

§ 371 Date: Dec. 29, 1997

§ 102(e) Date: Dec. 29, 1997

[87] PCT Pub. No.: WO97/01532

PCT Pub. Date: Jan. 16, 1997

[30] Foreign Application Priority Data

Jun. 28, 1995 [WO] WIPO .................. PCT/JP95/01290

[51] Int. Cl.$^6$ .................. C07C 255/40; C07C 255/41; A61K 31/275
[52] U.S. Cl. .................. 514/520; 514/525; 558/404; 558/405
[58] Field of Search .................. 558/404, 405; 514/520, 525

[56] References Cited

FOREIGN PATENT DOCUMENTS 0 761 215  3/1997  European Pat. Off. .

Primary Examiner—Alan L. Rotman
Attorney, Agent, or Firm—Oblon, Spivak, McClelland, Maier & Neustadt, P.C.

[57] ABSTRACT

The present invention is directed to a ketonitrile derivative represented by the following formula (1):

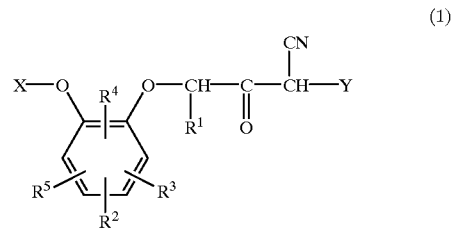

(wherein $R^1$ is a hydrogen atom or a lower alkyl group; each of $R^2$, $R^3$, $R^4$, and $R^5$, which may be identical to or different from each other, is a hydrogen atom, a halogen atom, a nitro group, a lower alkyl group, a lower alkoxyl group, or a substituted or unsubstituted phenoxy group; X is a substituted or unsubstituted aromatic hydrocarbon group or a substituted or unsubstituted heterocyclic group; Y is a substituted or unsubstituted aromatic hydrocarbon group, a substituted or unsubstituted heterocyclic group, a carbonyl group that has been substituted by a substituted or unsubstituted aromatic hydrocarbon group, a carbonyl group that has been substituted by a substituted or unsubstituted heterocyclic group, an N,N-di-substituted carbamoyl group, or an alkyl group that has been substituted by a heterocyclic group) or a salt thereof, and to an antibacterial agent as well as to a drug containing, as the effective ingredient, the ketonitrile derivative or the salt. This compound exhibits excellent antibacterial activity against gram-positive bacteria and gram-negative bacteria.

9 Claims, No Drawings

KETONITRILE DERIVATIVES AND ANTIBACTERIAL AGENT AND DRUGS CONTAINING THE SAME

This application is a 371 of PCT JP95/02751 filed Dec. 28, 1995.

TECHNICAL FIELD

The present invention relates to ketonitrile derivatives and drugs containing the derivatives. More particularly, the invention relates to compounds having antibacterial activities against gram-negative and gram-positive bacteria and to antibacterial agents and drugs containing the compounds.

BACKGROUND ART

In infectious diseases of humans, cattle, poultry, and fish caused by causal bacteria such as *Staphylococcus aureus*, hemolytic Streptococci, *Bacillus anthracis* and *Clostridium tetani*, antibiotics or synthetic antibacterial agents including penicillins, tetracyclines, macrolides, cephalosporins, and cephems have conventionally been used.

Prolonged terms of use or a large amount of use of these conventional antibiotics or synthetic antibacterial agents, however, causes drug resistance to the aforementioned causal bacteria. Especially, methicillin-resistant *Staphylococcus aureus* (MRSA), which causes a high death rate due to its strong toxicity, has become a big social problem, for it exhibits resistance to multiple drugs and makes therapy difficult.

The object of the present invention is to solve the aforementioned problem and to provide a compound having enhanced antibacterial activities against gram-negative bacteria and gram-positive bacteria, inter alia, gram-positive bacteria—such as Staphylococci—which have acquired drug resistance, as well as antibacterial compositions and drugs containing the compound.

The present inventors conducted extensive research to attain the above object, and found that certain ketonitrile derivatives having the below-described structure exhibit high antibacterial activities against gram-positive bacteria such as Staphylococci and Streptococci, as well as gram-negative bacteria, and that the derivatives are useful as drugs for the therapeutic treatment or prevention of a variety of infectious diseases and as antibacterial agents for diversified materials such as fibers, leading to completion of the invention.

DISCLOSURE OF THE INVENTION

The present invention provides a ketonitrile derivative represented by the following formula (1) or a salt thereof:

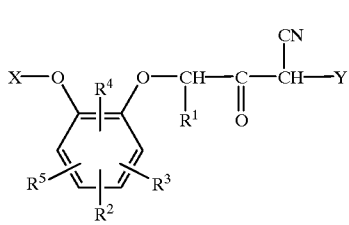

(1)

(wherein $R^1$ is a hydrogen atom or a lower alkyl group; each of $R^2$, $R^3$, $R^4$, and $R^5$, which may be identical to or different from each other, is a hydrogen atom, a halogen atom, a nitro group, a lower alkyl group, a lower alkoxyl group, or a substituted or unsubstituted phenoxy group; X is a substituted or unsubstituted aromatic hydrocarbon group or a substituted or unsubstituted heterocyclic group; Y is a substituted or unsubstituted aromatic hydrocarbon group, a substituted or unsubstituted heterocyclic group, a carbonyl group that has been substituted by a substituted or unsubstituted aromatic hydrocarbon group, a carbonyl group that has been substituted by a substituted or unsubstituted heterocyclic group, an N,N-di-substituted carbamoyl group, or an alkyl group that has been substituted by a heterocyclic group).

The present invention also provides a pharmaceutical composition and an antibacterial composition containing the above-described ketonitrile derivative (1) or a salt thereof and a carrier therefor.

The present invention also provides use, as a drug or an antibacterial agent, of the above-described ketonitrile derivative or a salt thereof.

The present invention further provides a method for the prevention and treatment of infectious diseases, characterized by administering an effective amount of the above-described ketonitrile derivative or a salt thereof.

The present invention still further provides an antibacterial construct to which the above-described ketonitrile derivative or a salt thereof is incorporated.

BEST MODES FOR CARRYING OUT THE INVENTION

In the present invention, the term "lower" generally indicates that the carbon number is from 1 to 5. Also, the carbon number of alkyl, alkoxyl, alkylthio, alkenyl, etc. is generally from 1 to 12 and preferably from 1 to 5.

In formula (1), examples of the lower alkyl groups represented by $R^1$ include linear or branched C1–C5 alkyl groups such as methyl, ethyl, propyl, and isopropyl. Preferably, $R^1$ is a hydrogen atom, a methyl group, or an ethyl group.

In formula (1), examples of $R^2$ through $R^5$ include a hydrogen atom; a halogen atom such as chlorine, bromine, fluorine, iodine, etc.; a nitro group; a lower alkyl group such as a methyl group, an ethyl group, a propyl group, a butyl group; a lower alkoxyl group such as a methoxy group, an ethoxy group, a propoxy group, etc.; and a phenoxy group such as 2-chloro-4-trifluoromethylphenoxy group.

In formula (1), examples of the unsubstituted aromatic hydrocarbon group represented by X include a phenyl group and a naphthyl group. Examples of the unsubstituted heterocyclic groups include groups constituted by 5-membered or 6-membered rings, each ring containing one or more hetero-atoms of oxygen, sulfur, or nitrogen; or groups which are formed by condensation of any of these groups and a benzene ring, for example, aromatic heterocyclic groups such as a pyridyl group, a quinolyl group, an isoquinolyl group, a quinoxalyl group, a pyrimidinyl group, an oxazolyl group, a benzoxazolyl group, a furyl group, a benzofuryl group, a thiazolyl group, a benzothiazolyl group, a thienyl group, or a benzothienyl group; and non-aromatic heterocyclic groups such as a piperidinyl group, a piperazinyl group, a pyrrolidinyl group, a morpholinyl group, a tetrahydrofuryl group, a tetrahydrothienyl group, and an oxanyl group. Of these groups, X is preferably an aromatic hydrocarbon group or an aromatic heterocyclic group.

Regarding the substituted aromatic hydrocarbon groups and substituted heterocyclic groups, examples of substituents include a halogen atom such as chlorine, fluorine, bromine, or iodine, a haloalkyl group such as a trifluoromethyl group, a nitro group, a cyano group, an alkyl group, an alkylthio group, and an alkoxycarbonyl group. These substituents may be present singly or plurally. Particularly, compounds substituted by one or two members—either homologous or heterologous—selected from the group consisting of a halogen atom and C1–C5 haloalkyl groups are preferred as they exhibit higher antibacterial activity.

Examples of more preferred species of X include a substituted or unsubstituted phenyl group, a substituted or unsubstituted naphthyl group, a substituted or unsubstituted pyridyl group, a substituted or unsubstituted benzoxazolyl group, a substituted or unsubstituted benzothiazolyl group, a substituted or unsubstituted thienyl group, a substituted or unsubstituted furyl group, a substituted or unsubstituted quinoxalyl group, a substituted or unsubstituted oxanyl group, and a hydrogen atom. Of these listed groups, more preferred groups are a phenyl group which may be substituted by a halogen atom, a haloalkyl group, or a cyano group; a naphthyl group which may be substituted by a halogen atom, a haloalkyl group, or a cyano group; a pyridyl group which may be substituted by a halogen atom, a haloalkyl group, or a cyano group; a benzoxazolyl group which may be substituted by a halogen atom, a haloalkyl group, or a cyano group; a benzothiazolyl group which may be substituted by a halogen atom, a haloalkyl group, or a cyano group; a thienyl group which may be substituted by a halogen atom, a haloalkyl group, or a cyano group; a furyl group which may be substituted by a halogen atom, a haloalkyl group, or a cyano group; a quinoxalyl group which may be substituted by a halogen atom, a haloalkyl group, or a cyano group; and an oxanyl group. Particularly preferably, X is a phenyl group which may be substituted by a halogen atom or a haloalkyl group; and a pyridyl group which may be substituted by a halogen atom or a haloalkyl group.

In formula (1), examples of the unsubstituted aromatic hydrocarbons represented by Y include a phenyl group and a naphthyl group. Examples of the unsubstituted hetorocyclic groups include groups constituted by 5-membered or 6-membered rings, each ring containing one or more heteroatoms of oxygen, sulfur, or nitrogen; or groups which are formed by condensation of any of these groups and a benzene ring, for example, heterocyclic groups exemplified for the aforementioned group X. Of these groups, Y is particularly preferably an aromatic hydrocarbon group and an aromatic heterocyclic group.

Regarding the substituted aromatic hydrocarbon groups, substituted heterocyclic groups, and carbonyl groups substituted by one of these groups, examples of substituents include a halogen atom such as chlorine, fluorine, bromine, or iodine, a haloalkyl group such as a trifluoromethyl group, an alkyl group, an alkoxyl group, an alkoxyalkyl group, an alkylthio group, and an alkoxycarbonyl group.

Examples of the N,N-di-substituted carbamoyl groups include carbamoyl groups that have been substituted by a substituted or unsubstituted alkyl group, alkenyl group, alkoxyl group, by a substituted or unsubstituted aromatic group, or by a substituted or unsubstituted heterocyclic group. Two substituents which are bonded to a carbamoyl group may be linked to each other to form a ring that may contain a hetero atom (e.g., a pyrrolidine ring, a piperidine ring, a piperazine ring, or a morpholine ring). For example, mention may be given of a 1-azacycloalkylcarbonyl group which may undergo condensation with a benzene ring or may be substituted by an alkyl group.

Examples of alkyl groups substituted by a heterocyclic group include C1–C5 alkyl groups which are substituted by a 5-membered or 6-membered heterocyclic group containing as a hetero atom an oxygen atom, a nitrogen atom, or a sulfur atom.

As regards Y, examples of preferred ones include a substituted or unsubstituted phenyl group, a substituted or unsubstituted pyridyl group, a substituted or unsubstituted pyrimidinyl group, a substituted or unsubstituted thienyl group, a substituted or unsubstituted naphthyl group, a substituted or unsubstituted benzoyl group, a substituted or unsubstituted furoyl group, a substituted or unsubstituted thenoyl group, tetrahydrofurylalkyl group, and an N,N-di-substituted carbamoyl group. Of these, more preferred are a phenyl group which may be substituted by a halogen atom, a haloalkyl group, an alkyl group, or an alkoxyl group; a pyridyl group which may be substituted by a halogen atom, a haloalkyl group, an alkyl group, or an alkoxyl group; a pyrimidinyl group which may be substituted by a halogen atom, a haloalkyl group, an alkyl group, or an alkoxyl group; a thienyl group which may be substituted by a halogen atom, a haloalkyl group, an alkyl group, or an alkoxyl group; a naphthyl group which may be substituted by a halogen atom, a haloalkyl group, an alkyl group, or an alkoxyl group; an N,N-di-substituted carbamoyl group which may be substituted by a lower alkyl group, a lower alkoxyalkyl group, an aryl group, or an aralkyl group; a 1-azacycloalkylcarbonyl group which may be condensed with a benzene ring or which may be substituted by an alkyl group; an oxoranyl-(C1–C5)alkyl group; a benzoyl group which may be substituted by a halogen atom, a haloalkyl group, an alkyl group, or an alkoxyl group; a furoyl group which may be substituted by a halogen atom, a haloalkyl group, an alkyl group, or an alkoxyl group; and a thenoyl group which may be substituted by a halogen atom, a haloalkyl group, an alkyl group, or an alkoxyl group. Of these groups, phenyl groups which may be substituted by a halogen atom, a haloalkyl group, an alkyl group, or an alkoxyl group are preferred.

Examples of the salts of the ketonitrile derivatives of formula (1) include inorganic salts formed with inorganic acids such as hydrochloric acid, sulfuric acid, nitric acid, hydrobromic acid, or phosphoric acid; organic salts formed with organic acids such as acetic acid, fumaric acid, maleic acid, lactic acid, tartaric acid, citric acid, malic acid, oxalic acid, methanesulfonic acid, benzenesulfonic acid, and p-toluenesulfonic acid; salts formed with acidic amino acids such as aspartic acid and glutamic acid; metal salts formed with metals such as sodium, potassium, calcium, magnesium, zinc, and silver; salts formed with organic bases such as dimethylamine, triethylamine, diethanolamine, and benzylamine; and salts formed with basic amino acids such as lysine and arginine. The present invention encompasses solvates of the ketonitrile derivatives (1) typified by hydrates.

The ketonitrile derivatives (1) of the present invention may be prepared, for example, according to any one of the following methods (a) to (e):

(a): A compound represented by formula (2) and a compound represented by formula (3) are reacted in the presence or absence of a solvent to obtain a ketonitrile derivative (1).

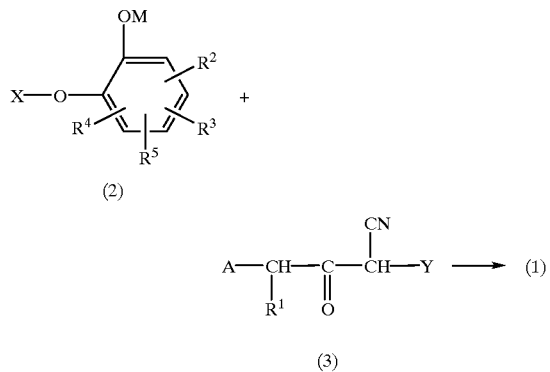

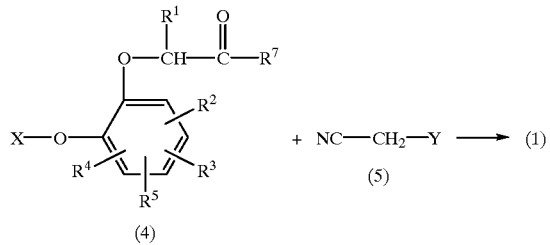

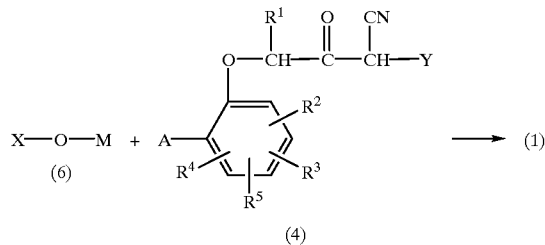

(wherein M is a hydrogen atom or an alkali metal, A is a halogen atom, and $R^1$, $R^2$, $R^3$, $R^4$, $R^5$, X, and Y have the same meanings as defined before).

(b): A compound represented by formula (4) and a compound represented by formula (5) are reacted in the presence or absence of a solvent to obtain a ketonitrile derivative (1).

(wherein $R^7$ is an alkoxyl group or a halogen atom, and $R^1$, $R^2$, $R^3$, $R^4$, $R^5$, X, and Y have the same meanings as defined before).

(c): A compound represented by formula (6) and a compound represented by formula (7) are reacted in the presence or absence of a solvent to obtain a ketonitrile derivative (wherein $R^1$, $R^2$, $R^3$, $R^4$, $R^5$, A, M, X, and Y have the same meanings as defined before).

(d): A compound represented by formula (8) and a compound represented by formula (9) are reacted in the presence or absence of a solvent to obtain a ketonitrile derivative (1).

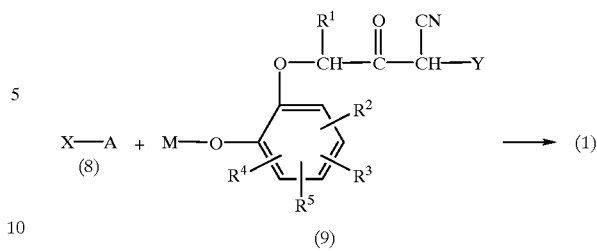

(wherein $R^1$, $R^2$, $R^3$, $R^4$, $R^5$, X, Y, A, and M have the same meanings as defined before).

(e): A compound represented by formula (10) and a compound represented by formula (11) are reacted in the presence or absence of a solvent to obtain a ketonitrile derivative represented by formula (1) in which Y is an N,N-di-substituted carbamoyl group.

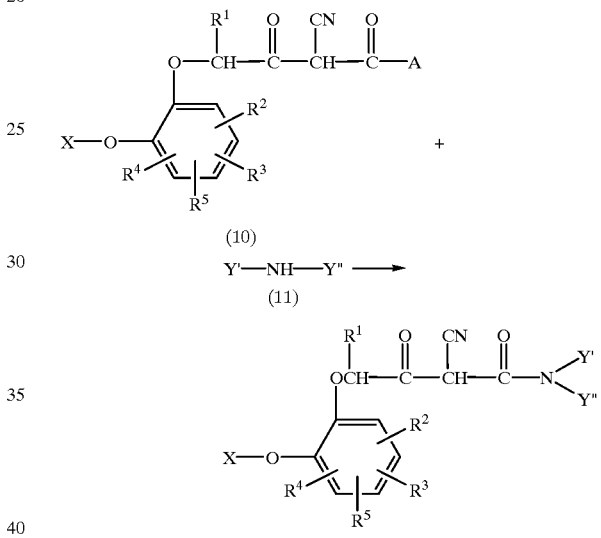

(wherein each of Y' and Y" represents a substituted or unsubstituted alkyl group, an alkenyl group, an alkoxy group, a substituted or unsubstituted aromatic group, or a substituted or unsubstituted heterocyclic group, in which Y' and Y" may link to each other to form a saturated or unsaturated ring which may contain a hetero atom, and $R^1$, $R^2$, $R^3$, $R^4$, $R^5$, X, Y, and A have the same meanings as defined before.)

Reaction solvents which are used in the above reaction schemes (a) to (e) are not particularly limited, and any known solvents may be used. Typical examples of solvents which are generally used as suitable ones include alcohols such as methanol and ethanol; ethers such as diethylether, dimethoxyethane, tetrahydrofuran, and dioxane; aromatic hydrocarbons such as benzene and toluene; chlorine-containing solvents such as methylene chloride, chloroform, and carbon tetrachloride; N,N-dimethylformamide, dimethylsulfoxide, and sulforane.

If necessary, a hydrogen halide scavenger is preferably present in the reaction system in order to remove hydrogen halide generated as a byproduct. The hydrogen halide scavenger is not particularly limited, and known ones for this purpose can be used. Typical and preferable examples of the hydrogen halide scavenger include trialkylamines such as triethylamine, trimethylamine, and tripropylamine; pyridine, sodium alcoholate, potassium alcoholate, DBU, sodium carbonate, potassium carbonate, sodium hydroxide, potassium hydroxide, and sodium hydride.

The reactions of reaction schemes (a) through (e) are preferably carried out at a temperature within the range of −30 to 200° C., particularly 5 to 150° C. The reaction time is from 0.5 to 45 hours, preferably 3 to 24 hours.

The ketonitrile derivatives are isolated from the reaction mixture and purified by known methods which are not particularly limited. In usual cases, the following procedure is preferably performed: The reaction mixture is first combined with water, followed by extraction with an organic solvent and subsequent removal of the solvent. The residue is purified by recrystallization or column chromatography.

Generally speaking, the ketonitrile derivatives (1) of the present invention are pale yellow or yellowish brown viscous matter or solid matter at normal ambient temperature and atmospheric pressure.

Of the thus-prepared compounds (1) of the present invention, preferable ones are the following compound Nos. 1 through 47. In the below-described formulas, those in which the position of a substituent(s) is/are not specified represent compounds having the substituent(s) at the 4-and/or 5-position(s) with respect to the group Y—CH(CN)—CO—CH(R$^1$)—O— on the benzene ring.

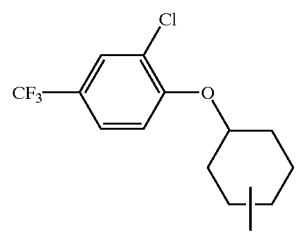

(1)

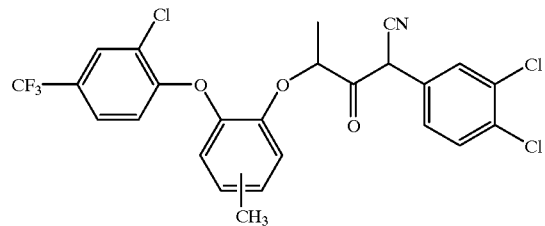

(2)

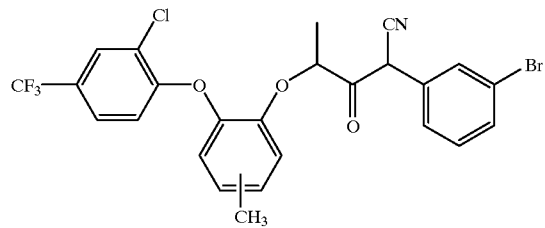

(3)

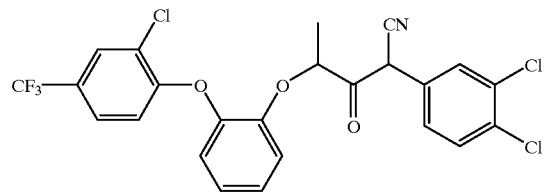

(4)

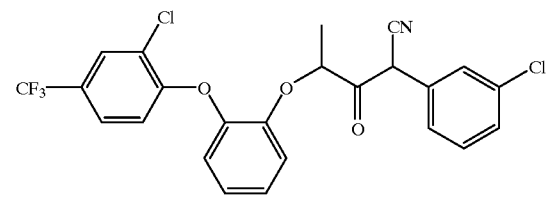

(5)

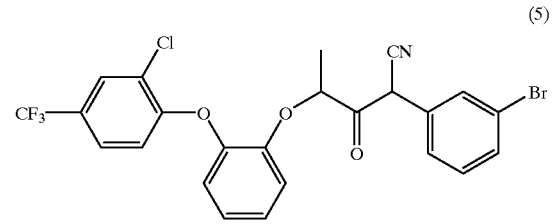

(6)

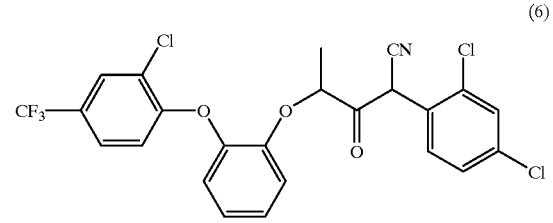

(7)

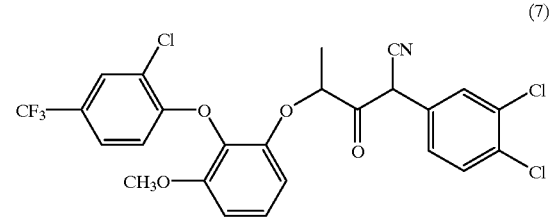

(8)

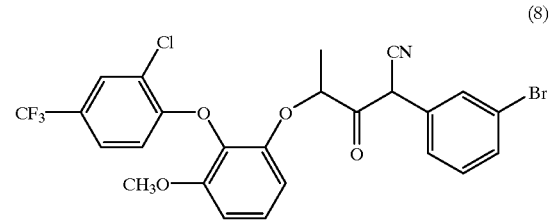

(9)

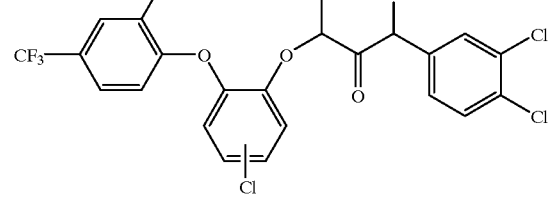

(10)

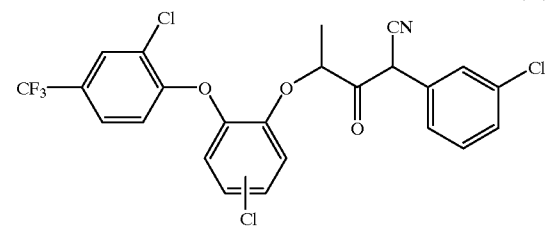

-continued

-continued

(25) (26) (27) (28) (29) (30) (31) (32) (33) (34) (35) (36) (37) (38)

(39) 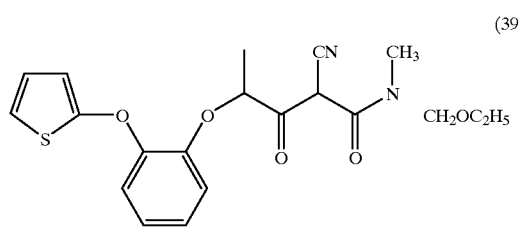

(40) 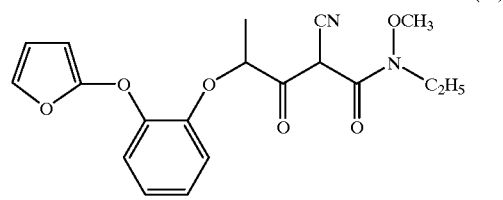

(41) 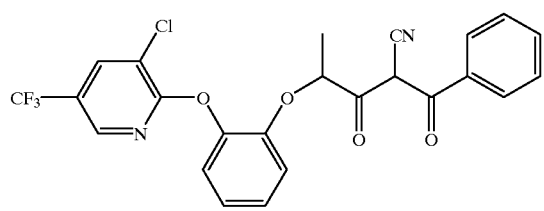

(42) 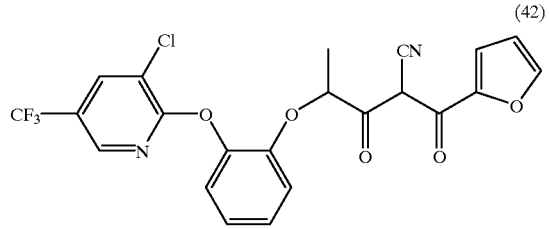

(43) 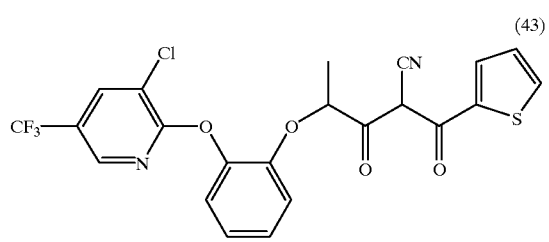

(44) 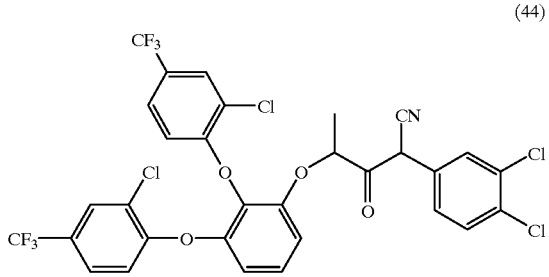

(45) 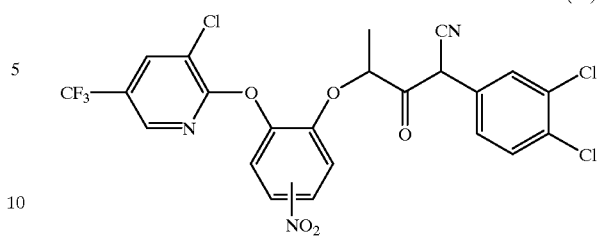

(46) 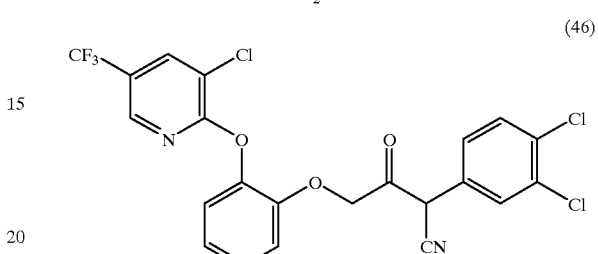

(47) 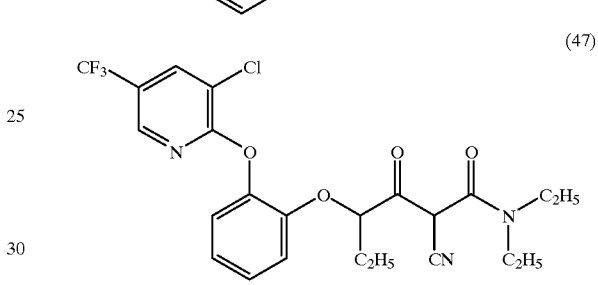

The compounds (1) of the present invention have low toxicity on mammals including humans, poultry, fish, etc. and exhibit excellent antibacterial activity against gram-positive and gram-negative bacteria. Therefore, the compounds are useful as drugs for the prevention and therapeutical treatment of various infectious diseases of humans and animals, and also as antibacterial agents applicable to diversified materials such as fibers.

The drugs of the present invention may be formed into various dosage forms and applied by various administration methods in accordance with the species of subjects to which the drugs are administered, i.e., mammals including humans, poultry, fish, etc.

When humans are the subjects, the drugs of the invention are administered orally or parenterally. In this case, the drugs may be arbitrarily formulated into preparations for oral use such as tablets, powders, granules, capsules, liquids, syrups, elixirs, and oil-base or aqueous suspensions; injections; preparations for topical use such as liquids, suspensions, emulsions, ointments, gels, creams, lotions, and sprays; and suppositories.

If the drugs are formed into solid preparations, pharmaceutically acceptable carriers for medicines, such as fillers, bulking agents, binders, disintegrants, solubilizers, wetting agents, excipients, and lubricants may be used.

If the drugs are formed into injections, the injection products may contain stabilizers, preservatives, tonicity agents, and solution adjuvants. Moreover, after the injection preparations are put in containers, they may be freeze-dried to turn them into solid products. They will be returned to injection liquids upon use. Although one dosage may be contained in one container, it is also possible that a plurality of dosages may be contained in one container.

When liquid preparations are formulated, they may contain suspending agents, emulsifying agents, or the like.

In order to administer the drugs of the present invention to mammals except humans, poultry, or fish, the drugs may be directly applied orally or may be combined with or dissolved in feed or drinking water. Alternatively, the drugs may be parenterally dosed by means of injection, per rectum administration, mammary administration, or medicated bath (in the case of fish). For these purposes, the drugs may be arbitrarily formed, for example, into powders, microgranules, soluble powders, syrups, liquids, injections, suppositories, and mammary injections as desired.

The dosage of the drugs of the present invention is 50 mg to 1 g, preferably 100 mg to 600 mg, per day for adult in cases of humans. When the drugs are administered to mammals except humans, poultry, or fish, the dosage differs depending on the purpose of administration (therapy or prophylactic treatment), species and size of the subject to be treated, types of bacteria which caused infection, and severity of the infection. Generally, the drugs are administered in amounts of 1–200 mg/day, preferably 5–100 mg/day per kg body weight at a single dose or in a divided dose from 2 to 4 times a day. For any case of humans, animals, and others, the dosage can be modified according to the conditions of the disease, age, and the body weight.

The drugs of the present invention exhibit enhanced antibacterial activities against bacteria which belong to the genus Staphylococcus, Streptococcus, Listeria, Bacillus, Clostridium, Corynebacteirum, Erysipelothrix, Bordetella, and Pasteurella.

Accordingly, the drugs of the present invention are effectively applicable to various diseases caused by the above bacteria including, for example, folliculitis, furuncle, carbuncle, erysipelas, lymphangitis/lymphonoditis, abscess, hidradenitis, marginal abscess, mastitis, superficial secondary infections associated with wounds, burns, or operative wounds, bronchitis, pneumonia, pyelonephritis, cystitis, urethritis, intrauterine infections, otitis media, sinuitis, endocarditis, sepsis, anthrax, and tetanus. The drugs of the invention are also effectively applicable to diseases of various infections of non-human animals including, for example, diseases of Staphylococcus and Clostridium infections of poultry, Streptococcus infections of pigs, erysipelas of pigs, Corynebacteirum infections and Clostridium infections of pigs, mastitis of cows, Clostridium infections of cows, cystitis and uterine abscess of dogs and cats, Streptococcus infections and Enterococcus infections of fish, and pseudotuberculosis of fish.

The compounds (1) of the present invention, exhibiting wide antibacterial spectra as mentioned above, can be used to impart antibacterial properties to fibers (e.g., fibers used for clothes and socks for medical purposes, fibers for bedclothes used for medical sheets; and fibers for fishing nets), paints (e.g., various paints for resin surfaces, floor paints, and paints for metals), various plastics, inks, etc. When the compounds (1) of the invention are used as antibacterial agents for these diversified materials, the compounds (1) may be formulated into antibacterial compositions together with a variety of carriers such as waxes, polymers, solvents, polymer emulsions, water, and surfactants.

Examples of the antibacterial constructs to which the compounds (1) of the present invention are incorporated include fibers and plastics treated with the above-mentioned antibacterial compositions. As means for the treatment of these materials with antibacterial compositions, mention may be given of application of the antibacterial composition onto the materials; kneading the antibacterial composition into the materials; soaking the materials in the antibacterial composition and drying; or spraying the antibacterial composition onto the materials.

EXAMPLES

The present invention will next be described in more detail by way of examples, which should not be construed as limiting the invention. In the following Preparation Examples, infrared absorption spectrum data are indicated with respect only to the characteristic absorption based on the ether bond and cyano group, and the mass spectrum data are of the molecular ion peaks ($M^+$) and fragments.

PREPARATION EXAMPLE 1

4-Methylcatechol (12.4 g) was dissolved in hexamethylphosphoramide. To the solution were added sodium hydride (oily state, 70%; 3.4 g), copper powder (3.0 g), and 3,4-dichlorobenzotrifluoride (21.5 g). The resultant mixture was stirred for 4 hours at 160° C. The copper powder was removed by filtration. Ether was added. The ether layer was washed with water, and subsequently ether was evaporated under reduced pressure to obtain a crude product. The crude product was purified by use of a silica gel column, to thereby obtain 2.6 g of a mixture of 2-(2-chloro-4-trifluoromethylphenoxy)-4-methyl phenol and 2-(2-chloro-4-trifluoromethylphenoxy)-5-methyl phenol. The mixture was dissolved in dimethylformamide, and to the resultant solution were added sodium hydride (0.34 g) and then methyl 2-chloropropionate (1.1 g). The mixture was stirred for 2 hours at 80° C. After the mixture was cooled, ether was added. The ether layer was washed with water, and subsequently ether was evaporated under reduced pressure to obtain a crude product. The crude product was purified by use of a silica gel column, to thereby obtain 2.2 g of a mixture of methyl 2-[2-(2-chloro-4-trifluoromethylphenoxy)-4-methylphenoxylpropionate and methyl 2-[2-(2-chloro-4-trifluoromethylphenoxy)-5-methylphenoxy]propionate. The mixture was dissolved in ethanol, and to the resultant solution were added 3,4-dichlorobenzylcyanide (1.1 g) and then sodium ethoxide prepared from metallic sodium (0.4 g). The mixture was refluxed with heat for 3 hours. After the mixture was cooled, ether was added. The ether layer was washed with water, and subsequently ether was evaporated under reduced pressure to obtain a crude product. The crude product was purified by use of a silica gel column, to thereby obtain 0.5 g of a mixture of 4-[2-(2-chloro-4-trifluoromethylphenoxy)-4-methylphenoxy]-2-(3,4-dichlorophenyl)-3-oxopentanonitrile and 4-[2-(2-chloro-4-trifluoromethylphenoxy)-5-methylphenoxy]-2-(3,4-dichlorophenyl)-3-oxopentanonitrile (Compound No. 1).

$^1$H-NMR(ppm): 8.0–6.3 (m, 10H, Ar), 5.6–4.5 (m, 2H, 2CH), 2.29,2.36(2s,3H,Ar—$CH_3$), 1.9–1.2(m,3H,$CH_3$). IR($cm^{-1}$): 2212 MS: 543, 329

PREPARATION EXAMPLE 2

2-methoxyphenol was synthesized from catechol (88 g) and methyl iodide (108 g). 2-Methoxyphenol (25 g) was dissolved in an aqueous solution of potassium hydroxide (13.3 g). The solution was dried by use of benzene and a Dean-Stark dehydration apparatus, and transformed into a phenoxide. The phenoxide was dissolved in sulforane. 3,4-dichlorobenzotrifluoride (44 g) was added thereto, and the mixture was stirred for 8 hours at 160° C. The mixture was subjected to extraction with ether and then purification on a silica gel column, to thereby obtain 2-(2-chloro-4-trifluoromethylphenoxy)methoxybenzene (7.0 g). This product was dissolved in 2,4,6-collidine, and was refluxed with heat for 7 hours together with lithium iodide (17 g). The mixture was subjected to extraction with ether and then to purification on a silica gel column, to thereby obtain 5.2 g of 2-(2-chloro-4-trifluoromethylphenoxy)phenol. This product was dissolved in dimethylformamide, and sodium hydride (0.7 g) was added. Subsequently, methyl 2-chloropropionate (3 g) was added and the mixture was stirred for 3 hours at 80° C. After cooled, the mixture was subjected to extraction with ether and then to purification on a silica gel column, to thereby obtain 6.7 g of methyl 2-[2-(2-chloro-4-trifluoromethylphenoxy)phenoxy]propionate. This product (2 g) and 3,4-dichlorobenzylcyanide (1 g) were refluxed with heat for 3 hours together with sodium ethoxide prepared from metallic sodium (0.4 g), followed by extraction with ether and purification on a silica gel column, to thereby obtain 1.1 g of 4-[2-(2-chloro-4-trifluoromethylphenoxy)-2-(3,4-dichlorophenyl)-3-oxopentanonitrile (Compound No. 3).

PREPARATION EXAMPLE 3

Catechol (55 g) was dissolved in a methanol solution of sodium methoxide prepared from metallic sodium (11.5 g). Methyl 2-chloropropionate (62 g) was added thereto and refluxed. Extraction with ether and purification on a silica gel column afforded 15 g of methyl 2-(2-hydroxyphenoxy)propionate. This product and 3,4-dichlorobenzylcyanide were dissolved in an ethanol solution of sodium ethoxide prepared from metallic sodium (7 g), and the mixture was refluxed with heat for 3 hours. Extraction with ether and purification on a silica gel column afforded 3 g of 2-(3,4-dichlorophenyl)-4-(2-hydroxyphenyl)-3-oxopentanonitrile. This compound (1 g), 2,3-dichloro-5-trifluoromethylpyridine (0.6 g), and potassium carbonate (0.4 g) were dissolved in dimethylformamide, and the mixture was stirred for 2 hours at 120° C. Extraction with ether and purification on a silica gel column afforded 0.6 g of 4-[2-(3-chloro-5-trifluoromethyl-2-pyridyloxy)phenoxy]-2-(3,4-dichlorophenyl)-3-oxopentanonitrile (Compound 18).

PREPARATION EXAMPLE 4

The spectrum data of Compound Nos. 2–21, 25, 28, 30, 34–36, and 44–47, which were prepared in a manner similar to that described in Preparation Examples 1 through 3, are shown below.

Compound No. 2
IR(cm$^{-1}$): 2212 MS: 553, 329 $^1$H-NMR (ppm): 7.9–6.3 (m, 10 H, Ar), 5.6–4.6 (m, 2H, 2CH), 2.29,2.36 (2s,3H,Ar—CH$_3$), 1.9–1.3(m,3H,CH$_3$).

Compound No. 3
IR(cm$^{-1}$): 2212 MS: 529,. 315 $^1$H-NMR(ppm): 8.0–6.3 (m,10H,Ar), 5.6–4.6 (m,2H,2CH), 1.9–1.2 (m,3H,CH$_3$).

Compound No. 4
IR(cm$^{-1}$): 2208 MS: 493, 315 $^1$H-NMR(ppm): 7.8–6.7 (m,11H,Ar), 5.7–4.3(m,2H,2CH), 1.9–1.0 (m,3H, CH$_3$).

Compound No. 5
IR(cm$^{-1}$): 2212 MS: 539, 315 $^1$H-NMR (ppm): 7.9–6.3 (m, 11H, Ar), 5.8–4.6 (m, 2H, 2CH), 1.8–1.2 (m,3H,CH$_3$);

Compound No. 6
IR(cm$^{-1}$): 2212 MS: 529, 315 $^1$H-NMR(ppm): 7.8–6.6 (m, 10H, Ar), 5.7–4.6 (m, 2H, 2CH), 1.8–1.2 (m,3H, CH$_3$).

Compound No. 7
IR(cm$^{-1}$): 2212 MS: 559, 345 $^1$H-NMR(ppm): 8.0–6.0 (m, 9H, Ar), 5.6–4.6 (m, 2H, 2CH), 3.89 (s, 3H, OCH$_3$), 1.9–1.2 (m,3H,CH$_3$).

Compound No. 8
IR(cm$^{-1}$): 2212 MS: 569, 345 $^1$H-NMR(ppm): 7.9–6.0 (m, 10 H, Ar), 5.8–4.6 (m, 2H, 2CH), 3.90 (s, 3H, OCH$_3$), 1.9–1.2 (m,3H,CH$_3$).

Compound No. 9
IR(cm$^{-1}$): 2212 MS: 563, 349 $^1$H-NMR(ppm): 8.2–6.3 (m,9H,Ar), 5.6–4.4 (m,2H,2CH), 1.9–1.2 (m,3H,CH$_3$).

Compound No. 10
IR(cm$^{-1}$): 2212 MS: 527, 349 $^1$H-NMR(ppm): 7.9–6.6 (m, 10H,Ar), 5.7–3.8 (m,2H,2CH), 1.8–1.1 ((m, 3H, CH$_3$).

Compound No. 11
IR(cm$^{-1}$): 2212 MS: 573, 349 $^1$H-NMR(ppm): 8.2–6.3 (m, 10H, Ar), 5.6–4.6 (m, 2H, 2CH), 1.9–1.2 (m, 3H, CH$_3$).

Compound No. 12
IR(cm$^{-1}$) : 2212 MS: 593, 371 $^1$H-NMR(ppm): 7.9–6.0 (m, 10H, Ar), 5.6–4.5 (m, 2H, 2CH), 1.9–1.2, 1.34 (m. s, 12H, CH$_3$,tert-Bu).

Compound No. 13
IR(cm$^{-1}$): 2212 MS: 583, 371 $^1$H-NMR(ppm): 8.0–6.0 (m, 9H,Ar), 5.6–4.6 (m,2H,2CH), 1.9–1.2, 1.35 (m,12H, CH$_3$,tert-Bu).

Compound No. 14
IR(cm$^{-1}$): 2208 MS:473, 315 $^1$H-NMR(ppm): 7.9–6.5 (m, 11H, Ar), 5.6–4.5 (m, 2H, 2CH), 2.35 (s,3H,Ar—CH$_3$), 1.8–1.0 (m, 3H,CH$_3$).

Compound No. 15
IR(cm$^{-1}$): 2212 MS: 489, 315 $^1$H-NMR(ppm): 7.9–6.8 (m, 11H, Ar), 5.7–4.4 (m, 2H, 2CH), 3.81 (s,3H,OCH$_3$), 1.8–1.0 (m,3H,CH$_3$).

Compound No. 16
IR(cm$^{-1}$): 2208 MS: 509, 315 $^1$H-NMR(ppm):8.2–6.5 (m, 14H, Ar). 5.7–4.5 (m, 2H, 2CH), 1.8–1.0 (m. 3H, CH$_3$).

Compound No. 17
IR(cm$^{-1}$): 2192 MS: 460, 315 $^1$H-NMR(ppm): 7.8–6.6 (m,10H, Ar), 5.7–4.6 (m,2H,2CH), 1.8–1.2 (m, 3H, CH$_3$).

Compound No. 18
IR(cm$^{-1}$): 2212 MS: 528, 316 $^1$H-NMR(ppm): 8.5–6.6 (m, 9H, Ar), 5.9–4.2 ((m, 2H, 2CH), 1.8–1.1 (m, 3H, CH$_3$).

Compound No. 19
IR(cm$^{-1}$): 2248 MS: 433, 349 $^1$H-NMR(ppm): 7.8–6.7 (m, 7H, Ar), 5.6–3.2 (m, 5H, 2CH, OCH, OCH$_2$), 2.1–1.2 (m, 9H, 3CH$_2$, CH$_3$).

Compound No. 20
IR(cm$^{-1}$): 2244 MS: 494, 315 $^1$H-NMR (ppm): 7.8–6.6 (m, 7H, Ar), 5.2–4.0 (m, 2H, 2CH), 3.8–3.0 (m,4H,2NCH$_2$), 2.0–1.1 (m,9H,3CH$_2$,CH$_3$).

Compound No. 21
IR(cm$^{-1}$): 2192 MS: 516, 315 $^1$H-NMR(ppm): 7.8–6.5 (m, 12H, Ar), 5.6–4.8 (m, 2H, 2CH), 3.5–2.8 (m,3H, NCH$_3$). 1.7–0.8 (m,3H, CH$_3$).

Compound No. 25
IR(cm$^{-1}$): 2212 MS: 462. 282 $^1$H-NMR(ppm): 8.3–6.2 (m, 10H, Ar), 5.8–4.5 (m, 2H, 2CH). 1.9–1.2 (m, 3H, CH$_3$).

Compound No. 28

IR(cm$^{-1}$): 2212 MS: 474, 309 $^1$H-NMR(ppm): 7.8–6.3 (m, 7H, Ar), 5.8–4.6 (m, 2H, 2CH), 3.7–3.2 (m, 4H, 2CH$_2$), 1.9–1.3 (m,7H,CH$_2$, CH$_3$).

Compound No. 30

IR(cm$^{-1}$): 2212 MS: 590, 299 $^1$H-NMR(ppm): 8.3–6.4 (m,18H, Ar), 5.6–3.2 (m,6H, 2CH, 2NCH$_2$), 1.9–1.2 (m,9H, 3CH$_2$, CH$_3$).

Compound No. 34

IR(cm$^{-1}$): 2212 MS: 480, 316 $^1$H-NMR(ppm):8.2–6.3 (m,8H, Ar), 5.6–4.4 (m,2H, 2CH), 2.4–2.2 (m,3H, Th—CH$_3$), 1.8–1.2 (m,s,3H, CH$_3$).

Compound No. 35

IR(cm$^{-1}$): 2212 MS: 543, 316 $^1$H-NMR(ppm): 8.1–6.2 (m,10H, Ar), 5.7–4.3 (m,2H, 2CH), 2.8–2.2 (m,4H, NCH$_2$, CH$_2$), 2.2–1.0 (m,5H, CH$_2$,CH$_3$).

Compound No. 36

IR(cm$^{-1}$): 2212 MS: 462, 281 $^1$H-NMR(ppm): 7.8–6.3 (M,8H, Ar), 5.7–4.6 (m,2H, 2CH), 3.4–2.9 (m,8H, morpholine), 1.8–1.2 (m,3H, CH$_3$).

Compound No. 44

IR(cm$^{-1}$): 2212 MS: 721, 509 $^1$H-NMR(ppm): 8.1–6.2 (m, 12H, Ar), 5.8–4.2 (m, 2H, 2CH), 1.8–1.2 (m,3H, CH$_3$).

Compound No. 45

IR(cm$^{-1}$): 2212 MS: 573, 361 $^1$H-NMR(ppm): 8.2–6.2 (m, 8H, Ar), 5.7–4.6 (m, 2H, 2CH), 1.9–1.2 (m,3H, CH$_3$).

Compound No. 46

IR(cm$^{-1}$): 2212 MS: 514, 316 $^1$H-NMR(ppm): 8.2–6.2 (m, 9H, Ar), 5.7–4.6 (m, 3H, CH$_2$, CH).

Compound No. 47

IR(cm$^{-1}$):2212 MS: 497, 316 $^1$H-NMR(ppm): 8.2–6.2 (m, 6H, Ar), 5.7–4.6 (m, 2H, 2CH), 3.2–2.4 (m, 6H, CH$_2$), 2.2–1.0 (m, 9H, CH$_3$).

TEST EXAMPLE 1

The minimum inhibitory concentration (MIC) was determined by an agar plate dilution method in accordance with the standard procedure authorized by Japan Chemotherapy Association ["Chemotherapy", 29, 76–79, 1981, under the heading "Revised Measurement of Minimum Inhibitory Concentration (MIC)"].

A suitable amount of each sample was dissolved in dimethylsulfoxide (DMSO) and subsequently diluted with the same amount of sterilized distilled water, to thereby prepare a bulk sample liquid of 1,000 μg/ml. Separately, bacterial cell suspensions (*Staphylococcus aureus* 209-P) to be used in the test were prepared in advance through culturing of the cells in Mueller-Hinton broth (DIFCO) at 37° C. overnight. Each of the cell suspensions, in which the final inoculation amount of bacteria was adjusted to 10$^6$CFU/ml, was inoculated to Muller-Hinton agar (DIFCO) containing the sample. The final sample concentrations were 100 μg/ml, 10 μg/ml, and 1 μg/ml.

Antibacterial activity was evaluated by measuring the inhibitory concentration (hereinafter abbreviated as IC) of bacterial growth after culturing at 37° C. for 18 hours. The IC values are shown in Table 1, wherein "≦100," "≦10," and "≦1" indicate that bacterial growth was inhibited at concentrations not more than 100 μg/ml, 10 μg/ml, and 1 μg/ml, respectively (the same rule applies correspondingly throughout the following Text Examples).

TABLE 1

Antibacterial activity against *Staphylococcus aureus* (209-P)

| Compound No. (IC*) | Compound No. (IC) |
|---|---|
| 1 (≦1) | 9 (≦1) |
| 2 (≦10) | 10 (≦10) |
| 3 (≦1) | 11 (≦10) |
| 4 (≦10) | 14 (≦100) |
| 5 (≦10) | 16 (≦100) |
| 6 (≦10) | 18 (≦10) |
| 7 (≦10) | 21 (≦100) |
| 8 (≦10) | |

*IC (Growth inhibitory concentration, μg/ml)

As is apparent from Table 1, all the tested samples effectively inhibited bacterial growth at a concentration of 100 μg/ml, and not a few tested samples inhibited bacterial growth at concentrations of 10 μg/ml and 1 μg/ml.

TEST EXAMPLE 2

Similar to Test Example 1, antibacterial activity was measured. The bacterium used in the test was *Staphylococcus aureus (TI*-1). The IC values are shown in Table 2.

TABLE 2

Antibacterial activity against *Staphylococcus aureus* (TI-1)

| Compound No. (IC*) | Compound No. (IC) |
|---|---|
| 1 (≦1) | 9 (≦1) |
| 2 (≦1) | 10 (≦1) |
| 3 (≦1) | 11 (≦1) |
| 4 (≦10) | 14 (≦100) |
| 5 (≦10) | 16 (≦100) |
| 6 (≦10) | 18 (≦10) |
| 7 (≦10) | 21 (≦100) |
| 8 (≦10) | |

*IC (Growth inhibitory concentration, μg/ml)

As is apparent from Table 2, all the tested samples effectively inhibited bacterial growth at a concentration of 100 μg/ml, and not a few tested samples inhibited bacterial growth at concentrations of 10 μg/ml and 1 μg/ml.

TEXT EXAMPLE 3

Similar to Test Example 1, antibacterial activity was measured. The bacterium used in the test was *Pasteurella multocida* (pig; Kobe-6). The IC values are shown in Table 3.

TABLE 3

Antibacterial activity against *Pasteurella multocida* (Kobe-6)

| Compound No. (IC*) | Compound No. (IC) |
|---|---|
| 1 (≦10) | 7 (≦100) |
| 2 (≦10) | 9 (≦100) |
| 3 (≦100) | 10 (≦100) |
| 4 (≦100) | 11 (≦100) |
| 5 (≦100) | 18 (≦100) |
| 6 (≦100) | |

*IC (Growth inhibitory concentration, μg/ml)

As is apparent from Table 3, all the tested samples effectively inhibited bacterial growth of a gram-negative bacterium *Pateurella multocida* at a concentration of 100 μg/ml.

TEST EXAMPLE 4

Similar to Test Example 1, antibacterial activity was measured. The bacterium used in the test was *Bordetella* bronchiseptica (SM2-4). The IC values are shown in Table 4.

TABLE 4

Antibacterial activity against *Bordetella bronchiseptica* (SM2-4)

| Compound No. (IC*) |
|---|
| 1 (≦100) |
| 9 (≦100) |

*IC (Growth inhibitory concentration, μg/ml)

As is apparent from Table 4, all the tested samples effectively inhibited bacterial growth of a gram-negative bacterium *Bordetella bronchiseptica* at a concentration of 100 μg/ml.

TEST EXAMPLE 5

Similar to Test Example 1, antibacterial activity was measured. The bacterium used in the test was *Escherichia coli* (NIHJ). The IC values are shown in Table 5.

TABLE 5

Antibacterial activity against *Escherichia coli* (NIHJ)

| Compound No. (IC*) | Compound No. (IC) |
|---|---|
| 3 (≦100) | 9 (≦100) |
| 4 (≦100) | 10 (≦100) |
| 5 (≦100) | 11 (≦100) |

*IC (Growth inhibitory concentration, μg/ml)

As is apparent from Table 5, all the tested samples effectively inhibited bacterial growth of a bacterium *Escherichia coli* at a concentration of 100 μg/ml.

TEST EXAMPLE 6

Similar to Test Example 1, antibacterial activity was measured. The bacterium used in the test was human-derived methicillin-resistant *Staphylococcus aureus* MRSA. The IC values are shown in Tables 6 and 7.

TABLE 6

Antibacterial activity against human-derived methicillin-resistant *Staphylococcus aureus* (MRSA)

| | Growth inhibitory concentration (IC; μg/ml) Compound No. | | | | | | | |
|---|---|---|---|---|---|---|---|---|
| Strain | 1 | 2 | 3 | 4 | 5 | 6 | 7 | 8 |
| 900056 | ≦1 | ≦1 | ≦10 | ≦10 | ≦10 | ≦10 | ≦10 | ≦10 |
| 891185 | ≦1 | ≦1 | ≦1 | ≦10 | ≦10 | ≦10 | ≦10 | ≦10 |
| 891192 | ≦1 | ≦1 | ≦1 | ≦10 | ≦10 | ≦10 | ≦10 | ≦10 |
| 891179 | ≦1 | ≦10 | ≦1 | ≦10 | ≦10 | ≦10 | ≦10 | ≦10 |

TABLE 7

| | Growth inhibitory concentration (IC; μg/ml) Compound No. | | | | | | |
|---|---|---|---|---|---|---|---|
| Strain | 9 | 10 | 11 | 14 | 16 | 18 | 21 |
| 900056 | ≦1 | ≦10 | ≦1 | ≦100 | ≦100 | ≦10 | ≦100 |
| 891185 | ≦1 | ≦10 | ≦1 | ≦100 | ≦100 | ≦10 | ≦100 |

TABLE 7-continued

| | Growth inhibitory concentration (IC; μg/ml) Compound No. | | | | | | |
|---|---|---|---|---|---|---|---|
| Strain | 9 | 10 | 11 | 14 | 16 | 18 | 21 |
| 891192 | ≦1 | ≦1 | ≦1 | ≦100 | ≦100 | ≦10 | ≦100 |
| 891179 | ≦1 | ≦1 | ≦1 | ≦100 | ≦100 | ≦10 | ≦100 |

As shown in Tables 6 and 7, with respect to some of the tested bacteria, Compound Nos. 1, 2, 3, 9, 10, and 11 exhibited an IC value of 1 μg/ml, and Compounds Nos. 4 through 8 and 18 exhibited an IC value of 10 μg/ml. Thus, all these compounds clearly exhibited strong antibacterial effects against MRSA.

TEST EXAMPLE 7

Similar to Test Example 1, antibacterial activity against fish-derived Enterococcus and Pasteurella bacteria was measured. The medium was supplemented with 1.5% NaCl, and the incubation temperature was set to 25° C. The IC values obtained are shown in Tables 8 and 9.

TABLE 8-1

Antibacterial activity against fish-derived pathogenic microorganism *Enterococcus seriolicida*

| | Growth inhibitory concentration (IC; μg/ml) Compound No. | | | | | | | |
|---|---|---|---|---|---|---|---|---|
| Strain | 1 | 2 | 3 | 4 | 5 | 6 | 7 | 8 |
| Enterococcus seriolicida MS89068 | ≦1 | ≦10 | ≦1 | ≦10 | ≦10 | ≦10 | ≦10 | ≦10 |
| Enterococcus seriolicida HI | ≦1 | ≦1 | ≦1 | ≦10 | ≦1 | ≦10 | ≦10 | ≦10 |
| Enterococcus seriolicida SE94-001 | ≦1 | ≦10 | ≦1 | ≦10 | ≦10 | ≦10 | ≦10 | ≦10 |
| Enterococcus seriolicida SE94-002 | ≦1 | ≦10 | ≦1 | ≦10 | ≦10 | ≦10 | ≦10 | ≦10 |
| Enterococcus seriolicida SE94-003 | ≦1 | ≦10 | ≦1 | ≦10 | ≦10 | ≦10 | ≦10 | ≦10 |
| Enterococcus seriolicida SE94-004 | ≦1 | ≦10 | ≦1 | ≦10 | ≦10 | ≦10 | ≦10 | ≦10 |
| Enterococcus seriolicida SE94-093 | ≦1 | ≦10 | ≦1 | ≦10 | ≦10 | ≦10 | ≦10 | ≦10 |
| Enterococcus seriolicida SE94-098 | ≦1 | ≦10 | ≦1 | ≦10 | ≦10 | ≦10 | ≦10 | ≦10 |
| Enterococcus seriolicida SE94-100 | ≦1 | ≦10 | ≦1 | ≦10 | ≦10 | ≦10 | ≦10 | ≦10 |
| Enterococcus seriolicida SE94-104 | ≦1 | ≦1 | ≦1 | ≦10 | ≦10 | ≦10 | ≦10 | ≦10 |
| Enterococcus seriolicida SE94-105 | ≦1 | ≦1 | ≦1 | ≦10 | ≦10 | ≦10 | ≦10 | ≦10 |
| Enterococcus seriolicida SE94-106 | ≦1 | ≦1 | ≦1 | ≦10 | ≦10 | ≦10 | ≦10 | ≦10 |

TABLE 8-2

Antibacterial activity against fish-derived pathogenic microorganism *Enterococcus seriolicida*

| | Growth inhibitory concentration (IC; μg/ml) Compound No. | | | | | | |
|---|---|---|---|---|---|---|---|
| Strain | 9 | 10 | 11 | 14 | 16 | 18 | 21 |
| *Enterococcus seriolicida* MS89068 | ≤1 | ≤1 | ≤1 | ≤100 | ≤100 | ≤10 | ≤100 |
| *Enterococcus seriolicida* HI | ≤1 | ≤1 | ≤1 | ≤100 | ≤100 | ≤10 | ≤100 |
| *Enterococcus seriolicida* SE94-001 | ≤1 | ≤1 | ≤1 | ≤100 | ≤100 | ≤10 | ≤100 |
| *Enterococcus seriolicida* SE94-002 | ≤1 | ≤10 | ≤1 | ≤100 | ≤100 | ≤10 | ≤100 |
| *Enterococcus seriolicida* SE94-003 | ≤10 | ≤1 | ≤1 | ≤100 | ≤100 | ≤10 | ≤100 |
| *Enterococcus seriolicida* SE94-004 | ≤10 | ≤1 | ≤1 | ≤100 | ≤100 | ≤10 | ≤100 |
| *Enterococcus seriolicida* SE94-093 | ≤1 | ≤10 | ≤1 | ≤100 | ≤100 | ≤10 | ≤100 |
| *Enterococcus seriolicida* SE94-098 | ≤1 | ≤1 | ≤1 | ≤100 | ≤100 | ≤10 | ≤100 |
| *Enterococcus seriolicida* SE94-100 | ≤1 | ≤1 | ≤1 | ≤100 | ≤100 | ≤10 | ≤100 |
| *Enterococcus seriolicida* SE94-104 | ≤1 | ≤1 | ≤1 | ≤100 | ≤100 | ≤10 | ≤100 |
| *Enterococcus seriolicida* SE94-105 | ≤1 | ≤1 | ≤1 | ≤100 | ≤100 | ≤10 | ≤100 |
| *Enterococcus seriolicida* SE94-106 | ≤1 | ≤1 | ≤1 | ≤100 | ≤100 | ≤10 | ≤100 |

TABLE 9

Antibacterial activity against fish-derived pathogenic microorganism *Pasteurella piscicida*

| | Growth inhibitory concentration (IC; μg/ml) Compound No. | | | |
|---|---|---|---|---|
| Strain | 1 | 2 | 18 | 21 |
| *Pasteurella piscicida* SP94-128 | ≤100 | ≤100 | ≤100 | ≤100 |
| *Pasteurella piscicida* SP94-175 | ≤100 | ≤100 | ≤100 | ≤100 |
| *Pasteurella piscicida* SP94-225 | ≤100 | ≤100 | ≤100 | ≤100 |
| *Pasteurella piscicida* SP94-151 | ≤100 | ≤100 | ≤100 | ≤100 |
| *Pasteurella piscicida* SP94-210 | ≤100 | ≤100 | ≤100 | ≤100 |
| *Pasteurella piscicida* SP94-219 | ≤100 | ≤100 | ≤100 | ≤100 |
| *Pasteurella piscicida* SP94-158 | ≤100 | ≤100 | ≤100 | ≤100 |
| *Pasteurella piscicida* SP94-174 | ≤100 | ≤100 | ≤100 | ≤100 |
| *Pasteurella piscicida* SP94-177 | ≤100 | ≤100 | ≤100 | ≤100 |
| *Pasteurella piscicida* SP94-209 | ≤100 | ≤100 | ≤100 | ≤100 |
| *Pasteurella piscicida* SP94-171 | ≤100 | ≤100 | ≤100 | ≤100 |
| *Pasteurella piscicida* SP94-101 | ≤100 | ≤100 | ≤100 | ≤100 |

As is apparent from Tables 8 and 9, all the tested samples listed in these tables effectively inhibited growth of different microorganism stains at a concentration of 100 μg/ml.

Formulation Example 1 (Capsules for humans):
The following ingredients were charged in capsules to prepare a capsule preparation.

| (Ingredients) | (Amounts, mg) |
|---|---|
| Compound No. 1 | 100 |
| Cornstarch | 23 |
| CMC-calcium | 22.5 |
| Hydroxymethylcellulose | 3 |
| Magnesium stearate | 1.5 |
| Total | 150.0 |

Formulation Example 2 (Powdery additive for feed):
The following ingredients were mixed to prepare a powdery additive for feed.

| (Ingredients) | (Amounts, g) |
|---|---|
| Compound No. 1 | 5–20 |
| Light silicic anhydride | 0.5 |
| Cornstarch | 84.5–79.5 |
| Total | 100.0 |

Industrial Applicability

As described hereinbefore, the compounds of the present invention possess excellent antibacterial activity against gram-positive and gram-negative bacteria. It is especially noteworthy that the compounds of the invention are effective against pathological Staphylococci including methicillin-resistant *Staphylococcus aureus* (MRSA). Therefore, the drugs according to the invention can be used in the prevention and therapeutical treatment of various infectious diseases of humans and animals including mammals except humans, as well as poultry, and fish caused by gram-positive bacteria or gram-negative bacteria. Moreover, the compounds of the present invention can be used as antibacterial agents for different materials such as fibers, paints, plastics, and ink.

We claim:

1. A ketonitrile derivative represented by the following formula (1) or a pharmaceutically acceptable salt thereof:

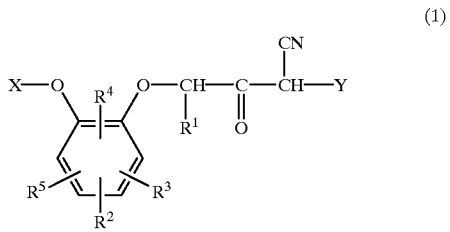

(1)

wherein $R^1$ is a hydrogen atom or a lower alkyl group; each of $R^2$, $R^3$, $R^4$, and $R^5$, which may be identical to or different from each other, is a hydrogen atom, a halogen atom, a nitro group, a lower alkyl group, a lower alkoxyl group, or a substituted or unsubstituted phenoxy group; X is a substituted or unsubstituted aromatic hydrocarbon group; and Y is a substituted or unsubstituted aromatic hydrocarbon group with a proviso that the terms $R^1$, $R^2$, $R^3$ and $R^4$ may represent no more than two nitro groups.

2. A compound of claim 1, wherein X is a phenyl group, a substituted phenyl group, a naphthyl group, or a substituted naphthyl group.

3. The compound of claim 1, wherein X is a phenyl group optionally substituted by a halogen atom, a haloalkyl group, or a cyano group; or X is a naphthyl group which may be substituted by a halogen atom, a haloalkyl group, or a cyano group.

4. The compound of claim 1, wherein X is a phenyl group substituted by a halogen atom or a haloalkyl group.

5. The compound of claim 1, wherein Y is a substituted or unsubstituted phenyl group.

6. The compound of claim 1, wherein Y is a phenyl group substituted by a halogen atom, a haloalkyl group, an alkyl group, or an alkoxy group; or X is a naphthyl group substituted by a halogen atom, a haloalkyl group, an alkyl group, or an alkoxyl group.

7. An antibacterial composition, comprising an effective amount of a compound of claim 1 in admixture with a carrier or excipient.

8. A pharmaceutical composition, comprising an effective amount of a compound of claim 1 in admixture with a pharmaceutically acceptable carrier.

9. A method for treating infectious disease, comprising administering to a patient in need thereof an effective amount of a compound of claim 1 in admixture with a pharmaceutically acceptable carrier.

* * * * *